US00PP17149P2

(12) United States Plant Patent
Austin

(10) Patent No.: US PP17,149 P2
(45) Date of Patent: Oct. 10, 2006

(54) SHRUB ROSE PLANT NAMED 'AUSVISIT'

(50) Latin Name: *Rosa hybrida*
Varietal Denomination: AUSvisit

(75) Inventor: David C. H. Austin, Wolverhampton (GB)

(73) Assignee: David Austin Roses, Ltd., Wolverhampton (GB)

( * ) Notice: Subject to any disclaimer, the term of this patent is extended or adjusted under 35 U.S.C. 154(b) by 0 days.

(21) Appl. No.: 11/048,011

(22) Filed: Jan. 31, 2005

(51) Int. Cl.
*A01H 5/00* (2006.01)

(52) U.S. Cl. ..... Plt./102

(58) Field of Classification Search ..... Plt./102, Plt./107, 130, 138, 141, 149
See application file for complete search history.

*Primary Examiner*—Howard J. Locker
(74) *Attorney, Agent, or Firm*—Klarquist Sparkman LLP

(57) ABSTRACT

Shrub rose plant suitable for cut flower production under greenhouse conditions, having deeply cupped, rich purple blooms, upright growth and strong Old Rose perfume.

1 Drawing Sheet

Genus and species: *Rosa hybrida.*
Variety denomination: 'AUSvisit'.

ORIGIN OF THE INVENTION

The present invention relates to a new and distinct variety of a shrub rose plant named 'AUSvisit' which was originated by me by crossing an unnamed, unpatented seedling with an unnamed, unpatented seedling.

BACKGROUND OF THE INVENTION

The primary objective of this breeding was to produce a rose plant suitable for year round cut flower production under standard greenhouse conditions having deep purple blooms with a strong Old Rose fragrance and a long vase life, produced on strong, upright stems.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deeply cupped, rich purple blooms.
2. Upright growth.
3. Strong Old Rose perfume.
4. Suitable for cut flower production under greenhouse conditions.

Asexual reproduction of this new variety by budding, as performed at Albrighton, England, shows that the foregoing and all other characteristics and distinctions come true to form and are established and transmitted through succeeding propagations.

COMPARISON WITH PARENTS

'AUSvisit' has deep purple blooms in the Old Rose style which differ from the seed parent's lilac/bush blooms of Hybrid Tea form and the crimson purple, smaller blooms of the pollen parent. The pollen parent also has more prickles than 'AUSvisit'.

COMPARISON WITH SIMILAR VARIETY

'AUSvelvet' (U.S. Plant Pat. No. 8,813) has fewer petals and is rich crimson in color.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at two years of age grown in a greenhouse environment at Albrighton, England.

Blooming habit: Continuous.
Bud:
*Size.*—About 2.6 cm long and 1.8 cm in diameter when the petals start to unfurl.
*Form.*—The bud form is pointed ovoid.
*Color.*—When sepals first divide, bud color is Red Group 53A. When half blown, the upper sides of the petals are Red-Purple Group 71C; and the lower sides of the petals are Red-Purple Group 72C.
*Sepals.*—Color: Upper surface: Green Group 143C and Yellow-Green Group 144B in patches. Lower surface: Green Group 143C. Length: 3.3 cm. Width: 0.8 cm. Shape: Elongated awl-shaped. Surface texture:

Upper surface: Pubescent. Lower surface: Smooth. There are three heavily appendaged sepals. There are two unappendaged sepals with canescent edges.

*Receptacle.*—Color: Yellow-Green Group 144C. Shape: Campanulate. Size: Medium, about 0.7 cm long×0.9 cm wide. Surface: Smooth.

*Peduncle.*—Length: Long, averaging about 12 cm. Surface: Prickly. Color: Yellow-Green Group 146A. Strength: Normal, slightly bending.

Bloom:

*Size.*—Large. Average open diameter is about 10.4 cm.

*Borne.*—In corymb shape clusters of two to three blooms. For cut flower production buds may be nipped out to leave a single bloom.

*Flowering stems.*—Strength: Strong. Average length is about 50 cm with a diameter of 5 mm. Number: 15–17.

*Form.*—When first open: Cupped. Permanence: Outer petal edges curl back.

*Petalage.*—Number of petals under normal conditions: 157.

*Color.*—The upper sides of the petals are Purple Group 77B blended with Red-Purple Group 67B. The reverse sides of the petals are Purple Group 77B blended with Red-Purple Group 67B. The bases of the petals are Yellow Group 10B. The major colors on the upper side are Purple Group 77B and Red-Purple Group 67B in equal measure.

*Variegations.*—None.

*Discoloration.*—The general tonality at the end of the first day: No change. At the end of the third day: Purple Group 77B. With further aging there is strong bluing.

*Fragrance.*—Strong, Old Rose.

Petals:

*Texture.*—Smooth.

*Size.*—Width: 4.8 cm. Length: 5.5 cm.

*Surface.*—Smooth.

*Shape.*—Broad, obovate. Margin: Entire, slightly undulating. Apex Shape: Emarginate. Base Shape: Rounded. Form: Flat, tips of mid to outer petals are slightly recurved.

*Arrangement.*—Quartered.

*Petaloids.*—Number: 24. Color: Red-Purple Group 67A.

*Persistence.*—Petals hang on and dry.

*Lastingness.*—On the plant: Long (about 5–7 days). As a cut flower: Long (about 5–7 days).

Reproductive parts:

*Stamens.*—Number: 44. Length: 7 mm. Anthers: Length: 3 mm. Color: Yellow-Orange Group 17C. Arrangement: Mixed with petaloids. Filaments: Color: Greyed-Red Group 180C. Length: 4 mm. Pollen: Color: Yellow-Orange Group 17C.

*Pistils.*—Number: 109. Length: 11 mm. Styles: Color: Red Group 54B. Length: 10 mm. Stigmas: Color: Greyed-Yellow Group 160B. Length: 1 mm.

*Hips.*—None observed.

PLANT

*Form.*—Shrub.

*Growth.*—Vigorous, upright, bushy.

*Age at maturity.*—One and one-half years.

*Mature plant.*—Height: 1.3 m. Width: 0.5 m.

*Rootstock.*—*Rosa multiflora inermis* for the observed plants.

Foliage: Number of leaflets on normal mid-stem leaves: 5, including terminal leaflet.

*Size.*—Large. About 16.1 cm long×15 cm wide.

*Quantity.*—Normal. Average number leaves per flowering stem: 7.

*Color.*—New foliage: Upper side: Yellow-Green Group 146A overlaid with Greyed-Red Group 178A. Lower side: Yellow-Green Group 144A overlaid with Greyed-Red Group 178A. Old foliage: Upper side: Green Group 139A. Lower side: Green Group N138B with red venation. The upper surface of new and old foliage is semi-glossy.

Leaflets:

*Size.*—About 8.9 cm long×5.2 cm wide.

*Shape.*—Broadly oval.

*Base shape.*—Rounded.

*Apex shape.*—Acuminate.

*Texture.*—Smooth.

*Edge.*—Serrated.

*Serrations.*—Double.

*Petiole.*—Color: Yellow-Green Group 152B.

*Petiole rachis.*—Color: Yellow-Green Group 152B. Underside: With prickles.

*Stipules.*—Length: 1.5 cm, glandular.

*Auricle shape.*—Linear.

*Disease resistance.*—Resistant to mildew, blackspot and rust under greenhouse growing conditions with average day-time temperature maintained at 17.5 degrees C.

*Pest resistance.*—Not tested.

*Vein color.*—Greyed-Orange Group 174B.

*Venation pattern.*—Reticulate.

Wood:

*New wood.*—Color: Greyed-Red Group 178A. Bark: Smooth.

*Old wood.*—Color: Yellow-Green Group 146A with a bronze tint. Bark: Smooth.

*Internode distance.*—6 cm.

Prickles:

*Quantity.*—On main canes from base: Ordinary, 18 per 5 cm stem length. On laterals from main canes: Few, 7 per 30 cm per stem length.

*Form.*—Hooked downward.

*Length.*—1.2 cm.

*Color when young.*—Yellow-Green Group 152B.

*Color when mature.*—Yellow-Green Group 152B with Greyed-Orange Group 176A at tip.

Small prickles:

*Quantity.*—On main stalks: Few. Number per stem length: 6 per 5 cm. On laterals: None.

*Color.*—When young: Yellow-Green Group 152B with Greyed-Orange Group 176A at tip. When mature: Grey-Brown Group 199C.

Winter hardiness: Not tested.

I claim:

1. A new and distinct variety of rose plant of the shrub class suitable for cut flower production under greenhouse conditions, substantially as herein shown and described, characterized particularly by its deeply cupped, rich purple blooms.; upright growth and strong Old Rose perfume.

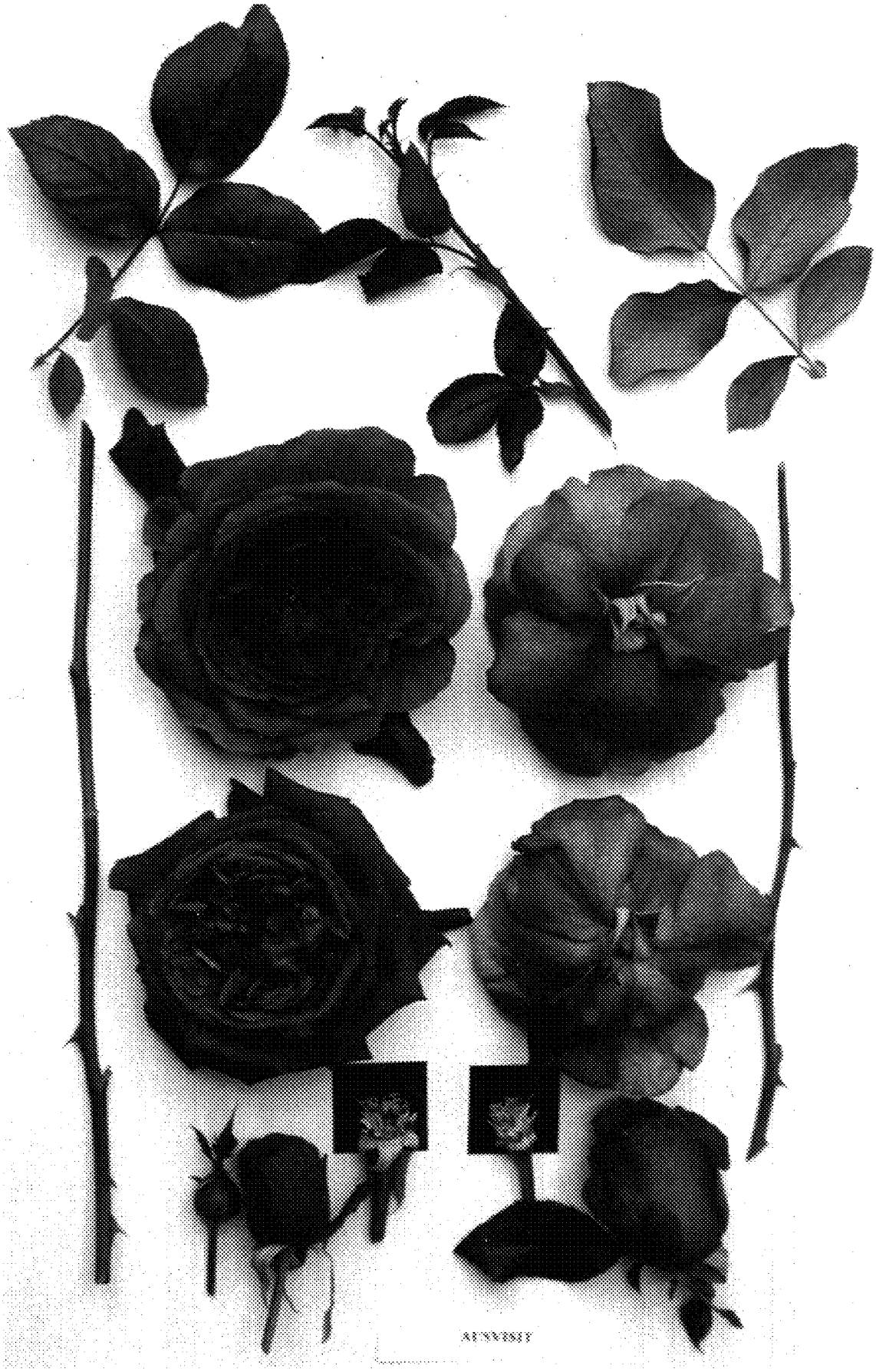

* * * * *